United States Patent [19]
Junek et al.
[11] 3,948,969
[45] Apr. 6, 1976

[54] 4-HYDROXYPHENYL-1,3-DIOXO-2-INDENYLIDENE ACETONITRILES

[75] Inventors: Hans Junek; Herwig Fischer-Colbrie, both of Graz, Austria

[73] Assignee: Lonza Ltd., Gampel, Valais, Switzerland

[22] Filed: Aug. 16, 1974

[21] Appl. No.: 498,115

[30] Foreign Application Priority Data
Aug. 20, 1973 Switzerland ....................... 11921/73

[52] U.S. Cl. ......... 260/465 F; 23/230 M; 23/230 R; 252/408
[51] Int. Cl.[2] ....................................... C07C 121/76
[58] Field of Search ................................. 260/465 F

[56] References Cited
OTHER PUBLICATIONS
Rappaport et al., J. Chem. Soc. Perkin II, pp. 1045–1052 (1973).

*Primary Examiner*—Lewis Gotts
*Assistant Examiner*—Dolph H. Torrence
*Attorney, Agent, or Firm*—Christen & Sabol

[57] ABSTRACT

A process for preparing a 4-hydroxyphenyl-1,3-dioxo-2-indenylidene-acetonitrile. The process includes reacting 2-dicyanomethylene-1,3-indanione with a phenol having the formula:

wherein $R_1$ and $R_2$ are the same or different and are each hydrogen, halogen, cyano, alkyl having one to four carbon atoms or alkoxy having one to four carbon atoms, at a temperature between 150° and 250°C. The reaction is preferably conducted in the presence of an organic solvent.

A 4-hydroxyphenyl-1,4-dioxo-2-indenylidene-acetonitrile having the formula:

wherein $R_1$ and $R_2$ are the same or different and are each hydrogen, halogen, cyano, alkyl having 1 to 4 carbon atoms or alkoxy having 1 to 4 carbon atoms. Such compounds are useful as indicators.

16 Claims, No Drawings

4-HYDROXYPHENYL-1,3-DIOXO-2-INDENYLIDENE ACETONITRILES

BACKGROUND OF THIS INVENTION

1. Field of This Invention

This invention relates to a process for producing 4-hydroxy-phenyl-1, 3-dioxo-2-indenylidene-acetonitrilies, to such compounds themselves and to the use of such compounds.

2. Prior Art

Indicator action utilizes the fact that certain compounds have different colors at different hydrogen ion concentrations. Such indicators find use in analytical chemistry.

A neutralization indicator is a substance which possesses different colors in acid and alkaline solutions.

Anthraquinone, which is colorless, is:

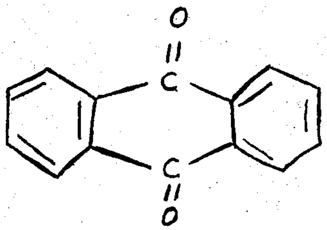

A number of the derivatives of anthraquinone are important in the dye industry, for example, as dye intermediates. The alizarin derivatives are mordant and acid dyes.

BROAD DESCRIPTION OF THIS INVENTION

This invention involves a process for preparing a 4-hydroxyphenyl-1,3-dioxo-2-indenylidene-acetonitrile. The process includes reacting 2-dicyanomethylene-1,3-indandione with a phenol having the formula:

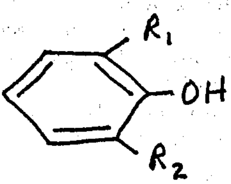

wherein $R_1$ and $R_2$ are the same or different and are each hydrogen, halogen, cyano, alkyl having one to four carbon atoms or alkoxy having one to four carbon atoms, at a temperature between 150° and 250°C. The reaction is conducted in the presence of an organic solvent. The preferred solvent is nitrobenzene. The solvent can constitute an excess of the phenol which participates in the reaction. Preferably the reaction is effected in a solvent boiling or refluxing at a temperature in excess of 180°C.

This invention also includes 4-hydroxyphenyl-1,4-dioxo-2-indenylidene-acetonitrile having the formula:

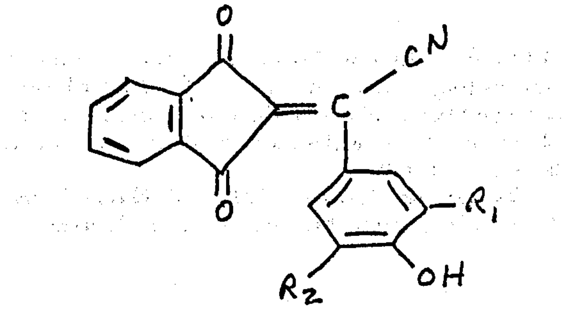

wherein $R_1$ and $R_2$ are the same or different and are each hydrogen, halogen, cyano, alkyl having 1 to 4 carbon atoms or alkoxy having 1 to 4 carbon atoms. Such compounds may be prepared by the process of this invention. Such compounds are useful as indicators.

The oxonol products of this invention have a yellow to ochre color and possess solvatochromic properties. While the oxonol products become a yellow to orange color in most solvents such as, methanol, ethanol, butanol, acetone, the oxonol products turn isopropanol a wine-red color. This allows them to be used to easily and quickly determine if isoproponal or a different solvent is contained in containers, vats, etc., in laboratories, industrial plants and the like. The oxonol products have useful indicating properties, and hence can be used in areas such as indicators in titrations. Alkalis cause a color change to violet. This color change disappears with acidification and reappears when treated with bases. This color change occurs at a pH to 6 to 9.

DETAILED DESCRIPTION OF THIS INVENTION 2-dicyanomethylene-1,3-indandione is:

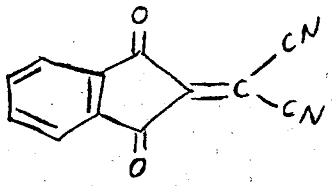

It can also be termed 2-dicyanomethylene-hydrindene-1, 3-one.

$R_1$ as used herein, can be hydrogen, halogen (i.e., chlorine, bromine, iodine or fluorine), cyano, alkyl having one to four carbon atoms or alkoxy having one to four carbon atoms. Examples of useful alkyls are methyl, ethyl, propyl, isopropyl, butyl, isobutyl, and tert.- butyl. Examples of useful alkoxys are methoxy, ethoxy, propoxy, isopropoxy, butoxy, isobutoxy, and tert.-butoxy.

$R_2$ as used herein, can be hydrogen, halogen (i.e., chlorine, bromine, iodine or fluorine), cyano, alkyl having one to four carbon atoms or alkoxy having one to four carbon atoms. Examples of useful alkyls are methyl, ethyl, propyl, isopropyl, butyl, isobutyl, and tert.- butyl. Examples of useful alkoxys are methoxy, ethoxy, propoxy, isopropoxy, butoxy, isobutoxy and tert.-butoxy.

$R_1$ and $R_2$ can be the same or different.

Examples of the phenol reactant or 2-$R_1$ substituted-6-$R_2$ substituted-phenol are o-cresol, phenol, o-bromophenol, guaiacol (i.e., o-methoxy-phenol), o-butoxyphenol, 2,6-dibromo-phenol, o-butyl-phenol, 2,6-dichloro-phenol, o-chloro-phenol, 2,6-diiodo-phenol, 2,6-dimethoxy-phenol, 2,6-xylenol, o-iodo-phenol, o-ethoxy-phenol, o-isopropyl-phenol, o-ethyl-phenol, o-propoxy-phenol, o-cyano-phenol and o-propylphenol.

The reaction of the phenol and 2-dicyanomethylene-1,3-indandione is preferably conducted in an organic solvent. The organic solvent must be liquid between 150° and 250°C. (or at least a portion thereof). Of course the solvent can also be liquid above 250°C. Preferably the reaction solvent boils at a temperature in excess of 180°C. Examples of such organic solvents are nitrobenzene (preferred), diphenyl, diphenyl methane, 2-nitrodiphenyl, diphenyl-p-tolyl-methane, 3-nitrodiphenyl, 1,1-diphenyl ethane, 4-nitrodiphenyl, 1,1,1-triphenyl ethane, 1,1,1,2-tetraphenyl ethane, 1,1,2-triphenyl ethane, 1,1,2,2-tetraphenyl ethane, triphenyl methane, 1,1,1-triphenyl propane, 1,2-dinitro benzene, 1,3-dinitro benzene, 1,3-diphenyl benzene, 1,4-dinitro benzene, 1-ethyl-2-nitro-benzene, 1-ethyl-3-nitro-benzene, 1-ethyl-4-nitro-benzene, 1,4-di-tert-butyl-benzene, 1-ethyl-4-isobutyl-benzene, hexaethyl benzene, 1,2,3,4-tetraethyl benzene, hexamethyl benzene, 1,2,3,5-tetraethyl benzene, isohexyl benzene, 1,2,4-triethyl benzene, pentaethyl benzene, 1,3,5-triethyl benzene, pentamethyl benzene, prehnitene, 2-benzyl-diphenyl, 2-methyl-diphenyl, 4-benzyl-diphenyl, 3-methyl-diphenyl, 2-nitro-diphenyl, 4-methyl-diphenyl, 3-nitro-diphenyl, o,o'-bitolyl, 4-nitro-diphenyl, o,m'-bitolyl, m,m'-bitolyl, and p,p'-bitolyl. The arylalkanes which are liquid between 150° and 250°C. (or at least a portion thereof) can be used as the reaction solvent. The nitrobenzenes, alkylbenzenes or alkylnitrobenzenes which are liquid between 150° and 250°C. (or at least a portion thereof) can be used as the reaction solvent.

The reaction solvent can be the phenol reactant itself, in which case a sufficient excess of the phenol is present to serve as the reaction solvent. The phenol can be used as the reaction solvent only if it is liquid between 150° and 250°C. (or at least portion thereof). The phenol used as the reaction solvent preferably boils at a temperature in excess of 180°C.

Except when the reaction solvent is an excess of the phenol reactant itself, the reaction solvent should be inert to the reactants and the product.

The reaction of this invention is conducted at a temperature between 150° and 250°C. and preferably at a temperature in excess of 180°C. The reaction also is preferably conducted at the reflux temperature of the particular reaction solvent being used, provided such a reflux temperature lies within the range of 150° and 250°C. (and preferably in excess of 180°C.).

The reaction of this invention can be conducted at atmospheric pressure and at pressures above and below atmospheric pressure.

The oxonol product can be purified by any convenient or conventional purification scheme.

The following examples illustrate this invention. As used throughout this specification and claims, all percentages, parts and ratios are on a weight basis unless otherwise stated or obvious to one ordinarily skilled in the art.

EXAMPLE 1

4-Hydroxyphenyl-1,3-dioxo-2-indenylidene-acetonitrile 0.5 gm of 2-dicyanomethylene-1,3-indandione and 0.5 gm of phenol were heated under reflux for one hour in 5 ml of nitrobenzene. After cooling, the deposit was filtered off and purified by repeated boiling in benzene. Small light brown stars were obtained with a yield of 29 percent. The product had a melting point of 278°C. (disintergration), an empirical formula of $C_{17}H_9NO_3$, and an analysis of:

| | C | H | N |
|---|---|---|---|
| Calculated | 74.18% | 3.30% | 5.08% |
| Obtained: | 74.47% | 3.43% | 5.73% |

EXAMPLE 2

3,5-Dichloro-4-hydroxyphenyl-1,3-dioxo-2-indenylidene-acetonitrile 0.5 gm of 2-dicyanomethylene-1,3-indandione and 0.6 gm of 2,6-dichlorophenol were converted and purified as indicated in Example 1. 0.4 gm of yellow needles having a melting point of 298°C. (disintegration) were obtained. This represented a yield of 47 percent. The product had an empirical formula of $C_{17}H_7NCl_2O_3$ and an analysis of:

| | C | H | N | C |
|---|---|---|---|---|
| Calculated: | 59.33% | 2.05% | 4.07% | 20.60% |
| Obtained | 60.22% | 2.20% | 4.60% | 19.98% |

The structure of the product was determined by means of IR, NMR and electron spectrum means.

EXAMPLE 3

Example 1 was repeated except that the solvent used was diphenyl. The oxonol product was obtained in high yield.

EXAMPLE 4

Example 2 was repeated except that no nitrobenzene was used as the solvent and 5 ml. of excess 2,6-dichlorophenol was used as the solvent. The oxonol product was obtained in high yield.

What is claimed is:

1. A 4-hydroxyphenyl-1,4-dioxo-2-indenylidene-acetonitrile having the formula:

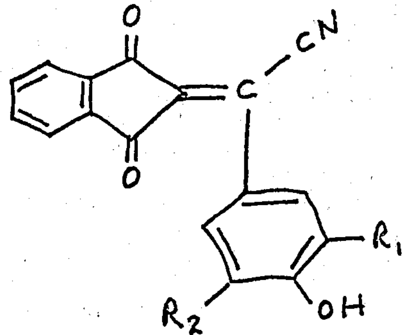

wherein $R_1$ and $R_2$ are the same or different and are each hydrogen, halogen, cyano, alkyl having 1 to 4 carbon atoms or alkoxy having 1 to 4 carbon atoms.

2. A compound as described in claim 1 wherein $R_1$ and $R_2$ are each cyano.

3. A compound described in claim 1 wherein $R_1$ and $R_2$ are each chlorine, bromine, iodine or fluorine.

4. A compound as described in claim 1 wherein $R_1$ and $R_2$ are each methyl, ethyl, propyl, isopropyl, butyl, isobutyl or tert.-butyl.

5. A compound as described in claim 1 wherein $R_1$ and $R_2$ are each methoxy, ethoxy, propoxy, isopropoxy, butoxy, isobutoxy or tert.-butoxy.

6. A 4-hydroxyphenyl-1,4-dioxo-2-indenylidene-acetonitrile having the formula:

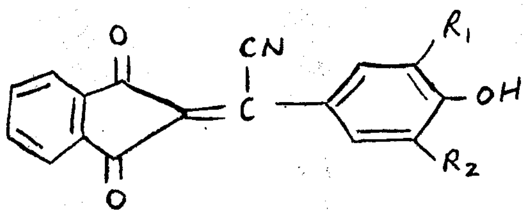

wherein $R_1$ and $R_2$ are each hydrogen or chlorine.

7. A compound as described in claim 6 wherein $R_1$ and $R_2$ are each hydrogen.

8. A compound as described in claim 6 wherein $R_1$ and $R_2$ are each chlorine.

9. A process for preparing a 4-hydroxyphenyl-1,3-dioxo-2-indenylidene-acetonitrile comprising reacting 2-dicyanomethylene-1,3-indandione with a phenol having the formula:

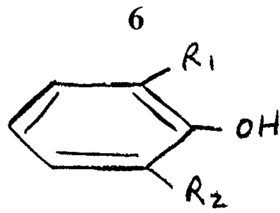

wherein $R_1$ and $R_2$ are the same or different and are each hydrogen, halogen, cyano, alkyl having one to four carbon atoms or alkoxy having one to four carbon atoms, at a temperature between 150° and 250°C. in the presence of an organic solvent.

10. A process as described in claim 9 wherein said solvent is nitrobenzene.

11. A process as described in claim 9 wherein said solvent is diphenyl.

12. A process as described in claim 9 wherein said solvent constitutes an excess of the phenol which participates in the reaction.

13. A process as described in claim 9 wherein said reaction is effected in a solvent boiling or refluxing at a temperature in excess of 180°C.

14. A process as described in claim 9 wherein said phenol is phenol.

15. A process as described in claim 9 wherein said phenol is 2,6-dichlorophenol.

16. A process as described in claim 9 wherein said solvent is a nitrobenzene, an alkylbenzene or an alkyl-nitrobenzene.

* * * * *